United States Patent [19]

Enderby

[11] 4,299,229
[45] Nov. 10, 1981

[54] METHOD OF OBSERVING THE AIM OR EFFECT OF A LASER BEAM ON A TARGET

[75] Inventor: Charles E. Enderby, Palo Alto, Calif.

[73] Assignee: Cavitron Corporation, New York, N.Y.

[21] Appl. No.: 100,595

[22] Filed: Dec. 5, 1979

[51] Int. Cl.³ .............................................. A61N 3/00
[52] U.S. Cl. .................................. 128/395; 356/318
[58] Field of Search ............... 128/395, 303.1; 356/73, 356/301, 318; 219/121

[56] References Cited

U.S. PATENT DOCUMENTS

| | | | |
|---|---|---|---|
| 3,096,767 | 7/1963 | Gresser et al. | 128/395 |
| 3,327,712 | 6/1967 | Kaufman et al. | 128/398 |
| 3,392,258 | 7/1968 | Bruma et al. | 219/121 |
| 3,417,754 | 12/1968 | Smart | 128/395 |
| 3,659,613 | 5/1972 | Bredemeier | 128/395 |
| 3,693,623 | 9/1972 | Harte et al. | 128/303.1 |
| 3,769,963 | 11/1973 | Goldman et al. | 128/395 X |
| 3,809,092 | 5/1974 | Abraham | 128/305 |
| 3,850,525 | 11/1974 | Kaye | 356/73 |
| 3,906,953 | 9/1975 | Wallace et al. | 128/303.1 |

*Primary Examiner*—John D. Yasko

[57] ABSTRACT

A method of observing the aim or effect of a laser beam on a target which fluoresces upon irradiation with a laser beam uses the laser beam to provide light for observing the target, but shields the observer from the laser beam. The method comprises irradiating with a laser beam a target which fluoresces upon exposure to the laser beam and blocking the reflected or scattered laser light from the observer while passing the light from the target fluorescence to the observer for viewing the aim or effect of the laser beam on the target.

11 Claims, 1 Drawing Figure

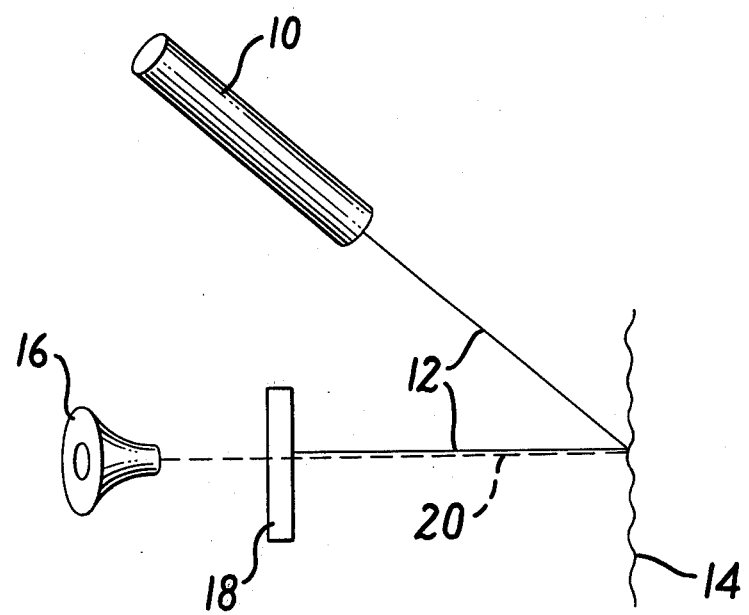

METHOD OF OBSERVING THE AIM OR EFFECT OF A LASER BEAM ON A TARGET

BACKGROUND OF THE INVENTION

The invention relates to a method of observing the aim or effect of a laser beam on a target.

Lasers have already found wide utility in industrial and medical operations, and new uses are continually being discovered. In many of these industrial and medical operations, however, the intensity of the laser beam which is required for the operation is harmful to observe. Government regulation of exposure to laser radiation by the U.S. Bureau of Radiological Health is one indication of the harm to an observer which can result from observing laser beams and the need to protect the observer from the laser beam.

The danger to the observer from the laser beam is readily understood in many industrial and medical operations in which the intended effect of the laser beam on the target is destructive. For example, carbon dioxide lasers have found medical utility because the laser wavelength is readily absorbed by water and thus can readily remove water-containing tissue. The desired tissue-removing function, however, also indicates that the aim and effect of the laser on the tissue which is to be removed cannot be observed while the laser beam is present because the portion of the laser beam which is reflected or scattered by the target would harm the observer's eye in the same way as it desireably removes tissue at the target.

Many laser devices therefore have a shutter which blocks the observer's view of the target while the laser beam is present to protect the observer. One such shutter arrangement, for example, is disclosed in the assignee's U.S. Pat. No. 3,659,613. The shutter in this patent is a rotating, segmented chopper disc having alternate segments which reflect the laser to the target and block the observer's view of the target and segments which allow observation of the target. The view-blocking segments of the chopper disc are rotated into operative position in synchronism with laser pulses to block each pulse but the pulses are provided at a frequency higher than is observable so that the appearance to the observer through the alternate segments is of a continuous view of the target. In fact, however, the actual aim and effect of the laser beam while the laser beam is present cannot be observed because the chopper disc shields the observer from the laser beam while the laser beam is present. Other shutter arrangements which are not synchronized to non-observable laser pulse frequencies are known, but even further impair the observer's view of the aim and effect of the laser.

Shutter arrangements which prevent the laser beam from being reflected or scattered from the target to the observer present still a further problem. Inasmuch as the laser light is blocked from the observer for protection, another source of light for observing the target while the laser beam is not present must be provided. Ambient light on the target is sometimes available to readily solve this problem, but in other industrial or medical operations the target may be shielded from ambient light to thus require a source of light other than the laser beam for observing the target. For example, laser beams have been directed inside human body cavities with fiber optics or articulated guides. The body about the target then shields the target from ambient light so that, when a shutter blocks the laser light, further arrangements for illuminating the target for observation have to be provided. One such target-illuminating arrangement is suggested in the assignee's before-mentioned U.S. Pat. No. 3,659,613, and another which is specifically directed to endoscopically illuminating a target inside a body is disclosed in the assignee's further U.S. Pat. No. 3,906,953. The apparatus for illuminating the laser targets for observation disclosed in these patents could be eliminated, however, if the light provided by the laser beam could also be used for observing the target without harm to the observer.

SUMMARY OF THE INVENTION

It is therefore an object of the invention to provide a method of observing the aim or effect of a laser beam on a target, and more particularly, a method of observing the aim or effect of the laser beam simultaneously with the presence of the laser beam.

It is another object of the invention to provide a method of observing the aim or effect of a laser beam on a target which uses the laser beam to provide light for observing the target.

To this end, the invention provides a method of observing a target which uses a laser beam which irradiates the target to provide light for observing the target, but shields the observer from at least the portion of the laser beam which would harm the observer. A target which fluoresces upon exposure to the laser beam at a wavelength different from that of the laser beam is irradiated with a laser beam. The different wavelength of the fluorescent light from the target upon laser beam irradiation is passed to the observer to provide light for observing the target while at least the portion of the laser beam which would harm the observer is blocked from the observer. The preferred way of transmitting the fluorescent light to the observer while blocking the laser beam is a band-blocking filter which blocks the wavelength or wavelengths of the laser beam, but passes the different wavelength(s) of the fluorescent light from the target.

One use of the method is in medical operations. Some ophthalmic tissues naturally fluoresce at a wavelength of approximately 5,800 Angstroms when irradiated with a laser beam having wavelengths centered at and close to about 5,000 Angstroms, for example an argon laser beam having principal wavelengths at 4,880 and 5,145 Angstroms. A band-blocking filter which blocks wavelengths of from, for example 4,800 to 5,200 Angstroms will then block at least the principal wavelengths of the laser beam, and any laser light in wavelength side bands immediately adjacent and beyond the principal wavelengths for safety, but pass the different wavelength of the fluorescence to the observer for viewing the target.

Other tissues which do not fluoresce or fluoresce insufficiently or fluoresce at a wavelength which is too close to that of the laser can be caused to fluoresce sufficiently at a wavelength sufficiently different from that of the laser beam by the addition of an appropriately fluorescing material to the tissue. For example, skin could be coated with a fluorescent material before irradiation with the laser beam. Fluorescent materials are, of course, well known so that one appropriate for the laser beam and blocking device (filter) can be selected as a mere matter of design. The enhancement of the fluorescence of the target in this way includes both providing the fluorescence with the added material and increasing the natural fluorescence of the target with a catalyst or other suitable agent.

The method has particular utility when light other than from the laser beam is not present at the target. For example, the method could be used when the laser beam is endoscopically directed to a target within a body which ambient light does not reach at least when the laser devices are positioned for directing the laser beam to the target. Further devices for illuminating the target sufficiently for observation of the aim and effect of the laser beam then are not needed although it may be necessary to provide a device which lowers the intensity of the laser beam to a level which will not affect tissue while the laser beam is being positioned, and then increases the laser intensity for tissue treatment.

In other specific uses of the method, it may be desirable to shield the target from ambient light which would allow the target to be observed without reliance on the fluoresce of the target. For example, it may be undesireable to expose certain light-sensitive tissues to ambient light sufficient for observing the tissue target. In these circumstances, again, the method which uses the fluorescence of the target to provide the light for observing the target will have particular utility. Both the circumstance in which the target is inherently shielded from ambient light as, for example, targets inside a body, and the circumstance in which non-laser light is intentionally excluded from the target are described herein as eliminating non-laser light from the target.

The need for shutters or other movable mechanical devices to protect the observer from the laser beam is also eliminated by the method. In the preferred form of the method in which a band-blocking filter is used to block the laser beam but transmit the fluorescent light, for example, only the filter is required. Construction and maintance expenses for an operating shutter are thus saved.

DESCRIPTION OF THE DRAWING

A preferred embodiment which is intended to illustrate but not to limit the method will now be described with reference to the drawing which shows, schematically, an arrangement for the practice of the method.

DESCRIPTION OF THE PREFERRED EMBODIMENT

As shown in the drawing, a laser 10 directs a laser beam 12 onto a target 14. Some of the laser beam 12 is reflected from the target toward the observer (not shown) who, in this preferred embodiment, observes the target through an eyepiece 16 which may contain various optical devices such as magnifying lenses. A filter 18 which blocks at least the portion of the laser beam which would harm the observer is, however, positioned between the eyepiece and the target to prevent the reflected laser beam from reaching the eyepiece. Specifically, the filter 18 is a band-blocking filter which blocks the wavelength of the laser beam and bands of wavelengths on either side of the center wavelength of the laser beam for safety.

The target 14, however, fluoresces when irradiated with the laser beam at a wavelength different from that of the laser beam. A ray 20 of the fluorescent light from the target is therefore shown as extending from the target through the filter to the eyepiece for observing the target, the different wavelength of the fluorescent light being outside the blocking band of the filter 18 to pass through the filter.

In the arrangement shown in the drawing, the laser beam 12 is shown as reflecting from the target; the illustrated reflection includes both spectral reflection and scattering of diffuse reflection. In another embodiment of the invention, however, the laser beam may pass through the target along with fluorescence from the side of the target opposite the laser 10 for observation. The method of the invention is clearly unaffected by the reflectance or transmittance mode of deriving the laser and fluorescent light from the target for the filter to block the laser beam, but transmit the fluorescence. Both are therefore included in the definition of a laser beam from the target as used here.

The laser 10 is an argon laser which emits a laser beam 12 having a center wavelength at approximately 5,000 Angstroms from a combination of blue and green light at principal wavelengths of 4,880 and 5,145 Angstroms. Certain ophthalmic tissues which are the target 14 naturally fluoresce upon irradiation with this laser beam at a center wavelength of approximately 5,800 Angstroms, a yellow light. The band-blocking filter 18 therefore is a filter which blocks blue-green light, but passes yellow light. Specifically, the filter 18 preferably blocks a band of from about 4,800 Angstroms to 5,200 Angstroms to block both the principal wavelengths of the laser and side bands beyond the highest and lowest principal wavelengths of about 200 Angstroms each. These bands are intended to be sufficiently wide to provide a margin of safety for blocking the laser beam while still passing the fluorescent light.

An alternative to the ophthalmic use of the method on naturally fluorescent tissue, which alternative is not now preferred because it has not been fully developed, but which may have utility, is the use of the method in dermatology. In such use, it is clear that the skin to be affected with the laser beam which may not fluoresce naturally sufficiently for effective use of the method can be coated with a fluorescent material. The wavelength of the fluorescence as well as that of the laser and that blocked by the filter can then be selected in the design of a system as described for the method to block the laser but pass the fluorescence. Such variation is contemplated as being within the scope of the invention.

In addition to other modifications and variations of the method as will occur to others in the art, it is also specifically contemplated as being within the scope of the invention that the eyepiece 16 may include known wavelength-changing devices or intensity-enhancing devices as would make possible the use of the invention with fluorescent light from the target outside the visable spectrum or fluorescence which is insufficiently strong for satisfactory observation of the target. Devices of both types are known and merely augment the utility of the method, but are not required by the method to require further description here.

I claim:

1. A method of observing the aim or effect of a laser beam on a target comprising the steps of:
   irradiating with a laser beam a target which fluoresces upon exposure to the laser beam at a wavelength different from that of the laser beam; and
   blocking from the observer at least a portion of the laser beam from the target which would harm the observer, but passing the light from the target fluorescence to the observer for viewing the aim or effect of the laser beam on the target.

2. A method as in claim 1 wherein the step of blocking the laser beam from the target but passing the fluorescent light from the target comprises filtering the light to the observer with a band-blocking filter which blocks the wavelength of the laser beam, but passes the fluorescent wavelength.

3. A method as in claim 1 or 2 wherein the step of blocking the laser beam further comprises blocking side bands of wavelengths immediately adjacent and beyond the longest and shortest principal wavelengths of the laser beam.

4. A method as in claim 3 wherein the step of blocking bands of wavelengths immediately adjacent each side of the center wavelength of the laser comprises blocking side bands of about 200 Angstroms.

5. A method as in claim 1, and further comprising the step of eliminating non-laser light from the target.

6. A method as in claim 1, 2, or 5 wherein the step of blocking from the observer at least a portion of the laser beam comprises blocking substantially all of the laser beam.

7. A method as in claim 1, 2, or 5 wherein the target is naturally fluorescent.

8. A method as in claim 1, 2, or 5; and further comprising the step of adding a material which enhances the fluorescence of the target to the target prior to irradiating the target with the laser beam.

9. A medical method of observing the aim or effect of a laser beam on a tissue target comprising the steps of:
   irradiating with a laser beam a tissue target which fluoresces upon exposure to the laser beam at a wavelength different from that of the laser beam; and
   filtering from the observer substantially all of the laser beam from the tissue target, but passing the different wavelength of the tissue target fluorescense to the observer for viewing the aim or effect of the laser beam on the tissue target.

10. A method as in claim 9; and further comprising the step of eliminating non-laser light from the tissue target.

11. A method as in claim 9 or 10; and further comprising the step of adding a material which enhances the fluorescense of the tissue target to the tissue target prior to irradiating the tissue target with the laser beam.

* * * * *